(12) United States Patent
Baker et al.

(10) Patent No.: US 9,750,726 B2
(45) Date of Patent: Sep. 5, 2017

(54) COMBINATIONS OF A MUSCARINIC RECEPTOR ANTAGONIST AND A BETA-2 ADRENORECEPTOR AGONIST

(71) Applicant: Glaxo Group Limited, Brentford, Middlesex (GB)

(72) Inventors: Darrell Baker, Middlesex (GB); Mark Bruce, Stevenage (GB); Glenn Crater, Mississauga (CA); Brian Noga, Durham, NC (US); Marian Thomas, Ware (GB); Patrick Wire, Durham, NC (US)

(73) Assignee: Glaxo Group Limited, Brentford, Middlesex (GB)

( * ) Notice: Subject to any disclaimer, the term of this patent is extended or adjusted under 35 U.S.C. 154(b) by 0 days.

(21) Appl. No.: 14/970,945

(22) Filed: Dec. 16, 2015

(65) Prior Publication Data

US 2016/0095840 A1    Apr. 7, 2016

Related U.S. Application Data

(63) Continuation of application No. 13/510,962, filed as application No. PCT/EP2010/068429 on Nov. 29, 2010, now abandoned.

(30) Foreign Application Priority Data

Dec. 1, 2009 (GB) .................................. 0921075.8

(51) Int. Cl.
| | | |
|---|---|---|
| A01N 43/00 | (2006.01) |
| A61K 31/33 | (2006.01) |
| A61K 31/439 | (2006.01) |
| A61K 31/138 | (2006.01) |
| A61K 45/06 | (2006.01) |
| A61K 9/00 | (2006.01) |
| B65D 75/36 | (2006.01) |

(52) U.S. Cl.
CPC .......... *A61K 31/439* (2013.01); *A61K 9/0075* (2013.01); *A61K 31/138* (2013.01); *A61K 45/06* (2013.01); *B65D 75/36* (2013.01)

(58) Field of Classification Search
CPC .............. A61K 2300/00; A61K 31/138; A61K 31/439; A61K 45/06
See application file for complete search history.

(56) References Cited

U.S. PATENT DOCUMENTS

| 6,537,983 | B1 | 3/2003 | Biggadike et al. |
|---|---|---|---|
| 6,759,398 | B2 | 7/2004 | Biggadike |
| 6,878,698 | B2 | 4/2005 | Biggadike et al. |
| 7,101,866 | B2 | 9/2006 | Biggadike et al. |
| 7,361,787 | B2 | 4/2008 | Box et al. |
| 7,439,393 | B2 | 10/2008 | Box et al. |
| 7,488,827 | B2 | 2/2009 | Laine et al. |
| 7,498,440 | B2 | 3/2009 | Laine et al. |
| 7,629,335 | B2 | 12/2009 | Biggadike et al. |
| 7,776,895 | B2 | 8/2010 | Box et al. |
| 7,982,067 | B2 | 7/2011 | Box et al. |
| 8,183,257 | B2 | 5/2012 | Laine et al. |
| 8,309,572 | B2 | 11/2012 | Laine et al. |
| RE44,874 | E | 4/2014 | Box et al. |
| 2009/0029901 | A1 | 1/2009 | Wood-Kaczmar |
| 2009/0298742 | A1 | 12/2009 | Roche et al. |
| 2011/0269970 | A1 | 11/2011 | Box et al. |
| 2012/0309725 | A1 | 12/2012 | Baker et al. |
| 2014/0113888 | A1 | 4/2014 | Crater |
| 2015/0313841 | A1 | 11/2015 | Jones |

FOREIGN PATENT DOCUMENTS

| WO | WO 03/024439 A1 | 3/2003 |
|---|---|---|
| WO | 2004110404 A1 | 12/2004 |
| WO | WO 2005/037280 A1 | 4/2005 |
| WO | WO 2005/046636 A1 | 5/2005 |
| WO | WO 2005/104745 A2 | 11/2005 |
| WO | 2005115462 A1 | 12/2005 |
| WO | 2005115464 A1 | 12/2005 |
| WO | 2005115465 A1 | 12/2005 |
| WO | 2005115466 A1 | 12/2005 |
| WO | 2005115467 A1 | 12/2005 |
| WO | WO 2005/115463 A1 | 12/2005 |
| WO | 2006062883 A2 | 6/2006 |
| WO | 2006062931 A2 | 6/2006 |
| WO | 2007012871 A1 | 2/2007 |
| WO | 2007068896 A1 | 6/2007 |
| WO | 2008012338 A2 | 1/2008 |
| WO | 2008021142 A2 | 2/2008 |
| WO | 2009036243 A1 | 3/2009 |
| WO | 2010038086 A2 | 4/2010 |
| WO | 2010072354 A1 | 7/2010 |
| WO | WO 2010/097114 A1 | 9/2010 |
| WO | WO 2010/097115 A1 | 9/2010 |
| WO | 2011067212 A1 | 6/2011 |
| WO | 2012168160 A1 | 12/2012 |
| WO | 2012168161 A1 | 12/2012 |

OTHER PUBLICATIONS

Jones P., *Aclidinium Bromide Twice Daily for the Treatment of Chronic Obstructive Pulmonary Disease: A Review*, Adv. Ther. (2013), vol. 30, No. 4, pp. 354-368.
Laine, et al. Journal of Medicinal Chemistry, 52(8): 2493-2505 (2009).
U.S. Appl. No. 12/353,436, filed Jan. 14, 2009.
U.S. Appl. No. 13/401,890, filed Feb. 22, 2012.
Fluticasone Drug information Online, Jun. 4, 2009.
Aaron, S. et al., "Tiotropium in Combination with Placebo, Salmeterol, or Fluticasone-Salmeterol for Treatment of Chronic Obstructive Pulmonary Disease. A Randomized Trial," Annals of Internal Medicine, pp. 545-556, W-144 , vol. 148 (8), Apr. 17, 2007 American College of Physicians.
Biggadike, K., "Letter" Clin. Resp. J. 5:3, 183-184 (2011) Print.

(Continued)

*Primary Examiner* — Jean Cornet
(74) *Attorney, Agent, or Firm* — James P. Riek; R. Steve Thomas; William R Majarian

(57) ABSTRACT

Combinations of a muscarinic acetylcholine receptor antagonist and a beta 2 agonist for inhaled administration via the nose or mouth, and methods of using them are provided.

17 Claims, No Drawings

(56) References Cited

OTHER PUBLICATIONS

EKLIRA™ GENUAIR™ inhalation powder—EU Authorization Product Characteristics.
Laine, D, et al., "The pre-clinical pharmacology of the inhaled muscarinic antagonist GSK573719 predicts once-daily clinical dosing" Eur. Resp. Socy. vol. 38 Issue Suppl 55 (Sep. 1, 2011).
Schelfhout, V. et al., Br. J. Clin. Pharmacol. 69:5,458-464 (2010).
TUDORZA™ PRESSAIR™—US FDA Approved Product Label.
Welte, T. et al., "Efficacy and Tolerability of Budesonide/Formoterol Added to Tiotropium in Patients with Chronic Obstructive Pulmonary Disease" Amer. J. Resp. & Critical Care Med. vol. 180, pp. 741-750 (2009).
FDA NDA 203975s003 lable Anoro Ellipta.
FDA Approval Letter Dec. 18, 2013—NDA 203975.
GSK Annual Report 2015.
Donohue, et al., "Magnitude of umeclidinium/vilanterol lung fuction effect depends on monotherapy responses: Results from two randomised controlled trials." Respiratory Medicines; 2016; vol. 112; pp. 65-74.
World Health Organization Fact Sheet No. 310, (Updated May 2014), http://www.who.int/mediacentre/factsheets/fs310/en/.
Allen et al., Fluticasone Furoate (FF) A Novel Inhaled Corticosteroid (ICS) Demonstrates Prolonged Lung Absorption Kinetics In Man. American Thoracic Society 2010 International Conference, Abstract D21 Asthma Therapy: New Targets, New Tricks. DOI: http://dx.doi.org/10.1164/ajrccm-conference.2010.181.1_MeetingAbstracts.A5408 (2010).
Allen et al., Fluticasone furoate, a novel inhaled corticosteroid, demonstrates prolonged lung absorption kinetics in man compared with inhaled fluticasone propionate. Clin Pharmacokinet. Jan. 2013;52(1):37-42.
Barnes, Triple inhalers for obstructive airways disease: will they be useful? Expert Rev Respir Med. Jun. 2011;5(3):297-300.
Cazzola et al., The scientific rationale for combining long-acting beta2-agonists and muscarinic antagonists in COPD. Pulm Pharmacol Ther. Aug. 2010;23(4):257-67.
Donohue et al., A randomized, double-blind dose-ranging study of the novel LAMA GSK573719 in patients with COPD. Respir Med. Jul. 2012;106(7):970-9.
Donohue et al., Efficacy and safety of once-daily umeclidinium/vilanterol 62.5/25 mcg in COPD. Respir Med. Oct. 2013;107(10):1538-46.
Forest Pharmaceuticals, Highlights of Prescribing Information, Tudorza Pressair. (2012).
GlaxoSmithKline, Evaluate the Safety, Efficacy and Dose Response of GSK573719 in Combination With Fluticasone Furoate in Subjects With Asthma (ILA115938). ClinicalTrials.gov Identifier NCT01573624, First Received Apr. 5, 2012, retrieved online at: https://clinicaltrials.gov/ct2/show/NCT01573624.
Peters et al., Tiotropium bromide step-up therapy for adults with uncontrolled asthma. N Engl J Med. Oct. 28, 2010;363(18):1715-26.
Response filed Apr. 14, 2015 to U.S. Office Action for U.S. Appl. No. 13/510,962, dated Jan. 14, 2015.
Response filed Apr. 15, 2016 to U.S. Office Action for U.S. Appl. No. 14/651,988, dated Feb. 25, 2016.
Response filed Aug. 20, 2014 to U.S. Office Action for U.S. Appl. No. 13/510,962, dated Jun. 20, 2014.
Response filed Jun. 21, 2013 to U.S. Office Action for U.S. Appl. No. 13/510,962, dated Jun. 10, 2013.
Response filed Mar. 10, 2014 to U.S. Office Action for U.S. Appl. No. 13/510,962, dated Oct. 9, 2013.
Response filed May 2, 2016 to U.S. Office Action for U.S. Appl. No. 14/124,276, dated Feb. 2, 2016.
Response filed Sep. 23, 2016 to U.S. Office Action for U.S. Appl. No. 14/651,988 dated Jun. 23, 2016.
U.S. Notice of Allowance for U.S. Appl. No. 14/651,988, dated Nov. 16, 2016.
U.S. Office Action for U.S. Appl. No. 13/510,962, dated Jan. 14, 2015.
U.S. Office Action for U.S. Appl. No. 13/510,962, dated Jun. 10, 2011.
U.S. Office Action for U.S. Appl. No. 13/510,962, dated Jun. 16, 2015.
U.S. Office Action for U.S. Appl. No. 13/510,962, dated Jun. 20, 2014.
U.S. Office Action for U.S. Appl. No. 13/510,962, dated Oct. 9, 2013.
U.S. Office Action for U.S. Appl. No. 14/124,276, dated Feb. 2, 2016.
U.S. Office Action for U.S. Appl. No. 14/124,276, dated Jul. 6, 2016.
U.S. Office Action for U.S. Appl. No. 14/651,988 dated Jun. 23, 2016.
U.S. Office Action for U.S. Appl. No. 14/651,988, dated Feb. 25, 2016.
U.S. Appl. No. 13/510,962, filed Aug. 20, 2012, Combinations of a Muscarinic Receptor Antagonist and a Beta-2 Adrenoreceptor Agonist.
U.S. Appl. No. 14/651,988, filed Jun. 12, 2015, Combination of Umeclidinium, Fluticasone Propionate and Salmeterol Xinafoate for Use in the Treatment of Inflammatory or Respiratory Tract Diseases.
Jones et al. Efficacy and safety of once-daily aclidinium in chronic obstructive pulmonary disease. Respiratory Research 2011, 12:55.
FDA Pulmonary Allergy Drugs Advisory Committee Meeting, Feb. 23, 2012, NDA 202-450: aclidinium bromide for the long-term, maintenance treatment of bronchospasm associated with chronic obstructive pulmonary disease (COPD), including chronic bronchitis and emphysema. (UMC292620). Retrieved from: https://www.fda.gov/downloads/AdvisoryCommittees/CommitteesMeetingMaterials/Drugs/Pulmonary-AllergyDrugsAdvisoryCommittee/UCM292620.pd.
Rosebraugh, Center for Drug Evaluation and Research, Approval Package for: Application No. 203975. Dec. 18, 2013.
FDA, U.S. Food & Drug Administration, TUDORZA™ PRESSAIR™—US FDA Approved Product Label. Retrieved online at: http://www.accessdata.fda.gov/scripts/cder/daf/index.cfm?event=BasicSearch.process (2012).
Fluticasone, www.Drugs.com, Wolters Kluwer Health (Wayback) (Jun. 4, 2009).

COMBINATIONS OF A MUSCARINIC RECEPTOR ANTAGONIST AND A BETA-2 ADRENORECEPTOR AGONIST

This application is a Continuation Application of U.S. patent application Ser. No. 13/510,962, filed Aug. 20, 2012, pending, which is a §371 national stage entry of International Patent Application No. PCT/EP2010/068429, filed 29 Nov. 2010, which claims priority to GB 0921075.8, filed Dec. 1, 2009, each of which are incorporated by reference herein in their entireties.

FIELD OF THE INVENTION

This invention relates to pharmaceutical products and compositions for use in the treatment of chronic obstructive pulmonary disease (COPD), asthma and related diseases.

More particularly this invention relates to the combination of a muscarinic receptor antagonist and a beta-2 adrenoreceptor agonist, and the use of said combination in treating diseases mediated via the $M_3$ muscarinic acetylcholine receptor and/or the beta-2 adrenoreceptor.

More particularly this invention is concerned with novel pharmaceutical combination products comprising 4-{(1R)-2-[(6-{2-[(2,6-dichlorobenzyl)oxy]ethoxy}hexyl)amino]-1-hydroxyethyl}-2-(hydroxymethyl)phenol triphenylacetate and 4-[hydroxy(diphenyl)methyl]-1-{2-[(phenylmethyl)oxy]ethyl}-1-azoniabicyclo[2.2.2]octane bromide and the use of said combination products in medicine, particularly in treating diseases mediated via the $M_3$ muscarinic acetylcholine receptor and/or the beta-2 adrenoreceptor, for example in the prophylaxis and treatment of inflammatory or respiratory tract diseases.

BACKGROUND OF THE INVENTION

Selective $\beta_2$-adrenoreceptor agonists have been used in the prophylaxis and treatment of clinical conditions for which a bronchodilating agent has been indicated. Such conditions include diseases associated with airflow obstruction such as chronic obstructive pulmonary diseases (COPD) (e.g. chronic and wheezy bronchitis, emphysema), asthma, respiratory tract infection and upper respiratory tract disease (e.g. rhinitis, including seasonal and allergic rhinitis).

In particular, asthma and other related disorders are typically treated with beta-2 adrenergic receptor agonists (beta-2 agonists) as they provide a bronchodilator effect to the patient, resulting in relief from the symptoms of breathlessness. Within the beta-2 agonist class there are presently available short acting compounds for immediate relief, such as salbutamol, biltolterol, pirbuterol and terbutaline. There are also longer acting compounds commercially available, such as salmeterol and formoterol. Salmeterol is available by prescription for use twice daily in the treatment of asthma.

Over the last two decades, inhaled anticholinergic agents have become well established as well-tolerated and effective bronchodilators for the treatment of COPD. Treatment with anticholinergics significantly improves $FEV_1$, (forced expiratory volume in 1 second) resting and dynamic lung hyperinflation, symptoms and exercise capacity, and reduces COPD exacerbations. Currently, only a few inhaled anticholinergic bronchodilators are available: the short-acting ipratropium bromide (ipratropium; dosed four-times-a-day) and oxitropium bromide, and the long-acting tiotropium bromide (tiotropium; dosed once-daily).

WO 03/024439 describes compounds of the general formula:

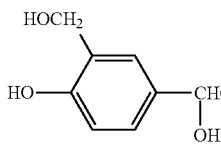

(I)

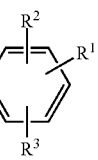

and salts, solvates, and physiologically functional derivatives thereof.

The compound 4-{(1R)-2-[(6-{2-[(2,6-dichlorobenzyl)oxy]ethoxy}hexyl)amino]-1-hydroxyethyl}-2-(hydroxymethyl)phenol is specifically described in WO03/024439, as are pharmaceutically acceptable salts thereof, in particular the acetate, triphenylacetate, α-phenylcinnamate, 1-naphthoate and (R)-mandelate salts.

WO2005/104745 describes compounds of the formulae:

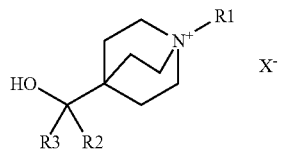

WO2005/104745 specifically describes the compound 4-[hydroxy(diphenyl)methyl]-1-{2-[(phenylmethyl)oxy]ethyl}-1-azoniabicyclo[2.2.2]octane bromide.

SUMMARY OF THE INVENTION

In a first aspect the present invention provides a novel pharmaceutical combination product comprising the therapeutic agents:

a) a compound of the formula:

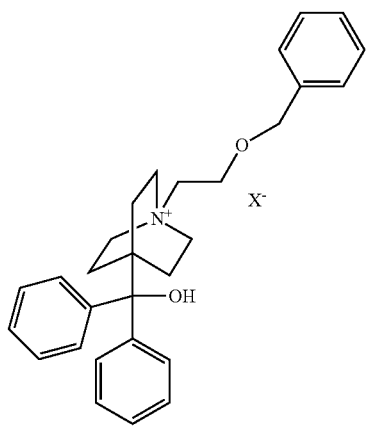

Compound (I)

wherein
X⁻ is a pharmaceutically acceptable anion;
and
b) a compound of the formula:

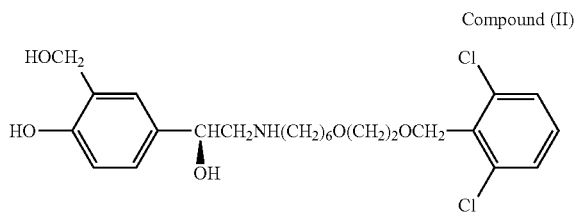

Compound (II)

or a pharmaceutically acceptable salt thereof.

Hereinafter, Compound (II) may refer to the free base depicted above, and/or one or more salts thereof, as dictated by the context.

In one embodiment the pharmaceutical combination product comprises 4-{(1R)-2-[(6-{2-[(2,6-dichlorobenzyl)oxy]ethoxy}hexyl)amino]-1-hydroxyethyl}-2-(hydroxymethyl)phenol triphenylacetate and 4-[hydroxy(diphenyl)methyl]-1-{2-[(phenylmethyl)oxy]ethyl}-1-azoniabicyclo[2.2.2]octane bromide.

In one embodiment 4-{(1R)-2-[(6-{2-[(2,6-dichlorobenzyl)oxy]ethoxy}hexyl)amino]-1-hydroxyethyl}-2-(hydroxymethyl)phenol triphenylacetate and 4-[hydroxy(diphenyl)methyl]-1-{2-[(phenylmethyl)oxy]ethyl}-1-azoniabicyclo[2.2.2]octane bromide are the sole active ingredients in said pharmaceutical combination product.

In another embodiment the pharmaceutical combination product of Compound (I) and Compound (II) additionally comprises an inhaled corticosteroid.

This invention also provides for use of the pharmaceutical combination product in the manufacture of a medicament for the treatment of conditions for which administration of one or more of the therapeutic compounds is indicated.

In one embodiment the use is for the manufacture of a medicament for the treatment of inflammatory or respiratory tract diseases, by simultaneous or sequential administration of Compound (I) and Compound (II).

In another embodiment the use is for the manufacture of a medicament for the treatment of chronic obstructive pulmonary disease (COPD) and/or asthma, by simultaneous or sequential administration of Compound (I) and Compound (II).

The invention also provides said pharmaceutical combination product for use in the treatment of inflammatory or respiratory tract diseases, such as chronic obstructive pulmonary disease (COPD) and/or asthma.

Another embodiment of the invention is a method for the treatment of inflammatory or respiratory tract diseases, comprising administering either sequentially or simultaneously, to a patient in need thereof, a pharmaceutical combination product comprising Compound (I) and Compound (II).

In one embodiment of the invention the inflammatory or respiratory tract disease is selected from the group consisting of chronic obstructive pulmonary disease, chronic bronchitis, asthma, chronic respiratory obstruction, pulmonary fibrosis, pulmonary emphysema, allergic rhinitis, small airways disease, bronchiectasis and cystic fibrosis.

In another embodiment of the invention the pharmaceutical combination product may be used for the treatment of inflammatory or respiratory tract diseases, and more specifically the treatment of chronic obstructive pulmonary disease (COPD) and/or asthma by simultaneous or sequential administration of Compound (I) and Compound (II).

DETAILED DESCRIPTION OF THE INVENTION

The present invention is directed to a pharmaceutical combination product comprising
a) a compound of formula:

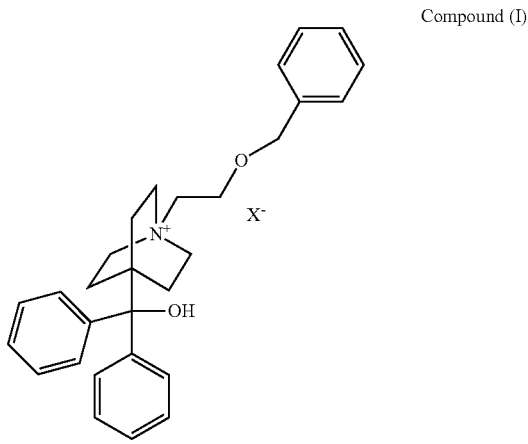

Compound (I)

wherein
X⁻ is a pharmaceutically acceptable anion;
and
b) a compound of formula:

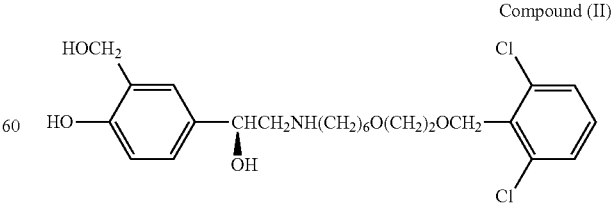

Compound (II)

or a pharmaceutically acceptable salt thereof.

The pharmaceutically acceptable anion depicted by X⁻ may be selected from chloride, bromide, iodide, hydroxide, sulfate, nitrate, phosphate, acetate, trifluoroacetate, fumarate, citrate, tartrate, oxalate, succinate, mandelate, methanesulfonate or p-toluenesulfonate. In one embodiment the pharmaceutically acceptable anion $X^-$ is bromide.

For purposes herein, the structural formula for the quaternary moiety (cation) of Compound (I) is also referred to as 4-[hydroxy(diphenyl)methyl]-1-{2-[(phenylmethyl)oxy]ethyl}-1-azoniabicyclo[2.2.2]octane.

In one embodiment of the invention Compound (I) is 4-[hydroxy(diphenyl)methyl]-1-{2-[(phenylmethyl)oxy]ethyl}-1-azoniabicyclo[2.2.2]octane bromide (also referred to herein as Compound (I) bromide).

Pharmaceutically acceptable acid addition salts of Compound (II) include those formed from hydrochloric, hydrobromic, sulphuric, citric, tartaric, phosphoric, lactic, pyruvic, acetic, trifluoroacetic, triphenylacetic, phenylacetic, substituted phenyl acetic eg. methoxyphenyl acetic, sulphamic, sulphanilic, succinic, oxalic, fumaric, maleic, malic, glutamic, aspartic, oxaloacetic, methanesulphonic, ethanesulphonic, arylsulponic (for example p-toluenesulphonic, benzenesulphonic, naphthalenesulphonic or naphthalenedisulphonic), salicylic, glutaric, gluconic, tricarballylic, mandelic, cinnamic, substituted cinnamic (for example, methyl, methoxy, halo or phenyl substituted cinnamic, including 4-methyl and 4-methoxycinnamic acid and α-phenyl cinnamic acid), ascorbic, oleic, naphthoic, hydroxynaphthoic (for example 1- or 3-hydroxy-2-naphthoic), naphthaleneacrylic (for example naphthalene-2-acrylic), benzoic, 4-methoxybenzoic, 2- or 4-hydroxybenzoic, 4-chlorobenzoic, 4-phenylbenzoic, bezeneacrylic (for example 1,4-benzenediacrylic) and isethionic acids.

In one embodiment the pharmaceutically acceptable salt of Compound (II) is selected from the acetate, 1-naphthoate and (R)-mandelate salts.

In another embodiment the pharmaceutically acceptable salt of Compound (II) is the α-phenylcinnamate salt.

In another embodiment the pharmaceutically acceptable salt of Compound (II) is the triphenylacetate salt.

The structural formula shown above for Compound (II) may be named as 4-{(1R)-2-[(6-{2-[(2,6-dichlorobenzyl)oxy]ethoxy}hexyl)amino]-1-hydroxyethyl}-2-(hydroxymethyl)phenol.

In one embodiment of the invention Compound (II) is 4-{(1R)-2-[(6-{2-[(2,6-dichlorobenzyl)oxy]ethoxy}hexyl)amino]-1-hydroxyethyl}-2-(hydroxymethyl)phenol triphenylacetate (also referred to as Compound (II) triphenylacetate).

In one embodiment the pharmaceutical combination product of the invention comprises 4-[hydroxy(diphenyl)methyl]-1-{2-[(phenylmethyl)oxy]ethyl}-1-azoniabicyclo[2.2.2]octane bromide and 4-{(1R)-2-[(6-{2-[(2,6-dichlorobenzyl)oxy]ethoxy}hexyl)amino]-1-hydroxyethyl}-2-(hydroxymethyl)phenol triphenylacetate.

In another embodiment the pharmaceutical combination product of Compound (I) and Compound (II) additionally comprises an inhaled corticosteroid, e.g. fluticasone propionate, mometasone furoate, budesonide or 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate).

In one embodiment said pharmaceutical combination product comprises 4-[hydroxy(diphenyl)methyl]-1-{2-[(phenylmethyl)oxy]ethyl}-1-azoniabicyclo[2.2.2]octane bromide, 4-{(1R)-2-[(6-{2-[(2,6-dichlorobenzyl)oxy]ethoxy}hexyl)amino]-1-hydroxyethyl}-2-(hydroxymethyl)phenol triphenylacetate and 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate).

In one embodiment, the pharmaceutical combination product of the invention comprises 4-[hydroxy(diphenyl)methyl]-1-{2-[(phenylmethyl)oxy]ethyl}-1-azoniabicyclo[2.2.2]octane bromide and 4-{(1R)-2-[(6-{2-[(2,6-dichlorobenzyl)oxy]ethoxy}hexyl)amino]-1-hydroxyethyl}-2-(hydroxymethyl)phenol triphenylacetate as the sole active ingredients.

Compound (I), specifically 4-[hydroxy(diphenyl)methyl]-1-{2-[(phenylmethyl)oxy]ethyl}-1-azoniabicyclo[2.2.2]octane bromide has been the subject of studies in animal models, and in humans, and has been found to be a long acting high-affinity pan-active muscarinic receptor antagonist which has potential for once-daily administration.

Compound (II), specifically 4-{(1R)-2-[(6-{2-[(2,6-dichlorobenzyl)oxy]ethoxy}hexyl)amino]-1-hydroxyethyl}-2-(hydroxymethyl)phenol and its salts has been extensively tested in animal and human studies and has been found to demonstrate sustained bronchodilation over a 24 hour period in conjunction with a favourable safety profile and thus has the potential for once-daily administration.

Compound (I) and Compound (II), and the combination thereof, are considered to have potential in the treatment of inflammatory or respiratory tract diseases such as chronic obstructive pulmonary disease, chronic bronchitis, asthma, chronic respiratory obstruction, pulmonary fibrosis, pulmonary emphysema, allergic rhinitis, small airways disease, bronchiectasis and cystic fibrosis.

COPD is a chronic disease characterised by airways obstruction and reduced maximum expiratory flow from the lungs that manifests as persistent daily symptoms, such as shortness of breath (dyspnoea), and limitation of the ability to perform daily activities or exertion. Furthermore, there are periodic exacerbations of the condition that result in worsening of the day-to-day symptoms and activity limitation, and can also lead to hospitalisation of the patient because of the severity of the worsening symptoms/limitation. In addition, there is a progressive decline in lung function (disease progression) over several years.

Bronchodilator treatment in COPD includes but is not necessarily limited to reducing symptoms, particularly dyspnoea, to allow a patient to undertake more daily activities and other activities that require exertion, and preventing exacerbations.

Asthma is a chronic condition, which is characterised by widespread, variable and reversible airflow obstruction. Symptoms include coughing, wheezing, breathlessness and/or a tight feeling in the chest. Asthma attacks are generally caused by exposure to a trigger, such as pollen, dust or other allergens, which causes constriction of the airways (bronchoconstriction). It will be appreciated that a subject suffering from a condition such as asthma, may variously from time to time display no overt symptoms of the condition, or may suffer from periodic attacks during which symptoms are displayed or may experience exacerbations or worsening of the condition. In this context the term 'treatment' is intended to encompass prevention of such periodic attacks or exacerbations of the existing condition. Such treatment may be referred to as 'maintenance treatment' or 'maintenance therapy'.

The amounts of Compound (I) and Compound (II), and in one embodiment of the invention, 4-[hydroxy(diphenyl)methyl]-1-{2-[(phenylmethyl)oxy]ethyl}-1-azoniabicyclo[2.2.2]octane bromide and 4-{(1R)-2-[(6-{2-[(2,6-dichlorobenzyl)oxy]ethoxy}hexyl)amino]-1-hydroxyethyl}-2-

(hydroxymethyl)phenol triphenylacetate, required to achieve a therapeutic effect will, of course, vary with the route of administration, the subject under treatment, the particular disorder or disease being treated, and the severity of the disease. In one embodiment, the route of administration is by inhalation via the mouth or nose. In a further embodiment, the route of administration is by inhalation via the mouth.

In one embodiment Compound (I), and specifically (4-[hydroxy(diphenyl)methyl]-1-{2-[(phenylmethyl)oxy]ethyl}-1-azoniabicyclo[2.2.2]octane bromide, may be administered by inhalation at a dose of from about 1 mcg to about 1000 mcg/daily, e.g. 100, 250 or 500 mcg per day. In a further embodiment, Compound (I) and specifically (4-[hydroxy(diphenyl)methyl]-1-{2-[(phenylmethyl)oxy]ethyl}-1-azoniabicyclo[2.2.2]octane bromide may be administered by inhalation at a dose of 62.5 mcg or 125 mcg per day. In general Compound (I) will be administered as a once-daily dose.

In a further embodiment, Compound (I), and specifically (4-[hydroxy(diphenyl)methyl]-1-{2-[(phenylmethyl)oxy]ethyl}-1-azoniabicyclo[2.2.2]octane bromide, may be administered by inhalation, once-daily, at a dose of 62.5 mcg per day.

In a further embodiment, Compound (I), and specifically (4-[hydroxy(diphenyl)methyl]-1-{2-[(phenylmethyl)oxy]ethyl}-1-azoniabicyclo[2.2.2]octane bromide, may be administered by inhalation, once-daily, at a dose of 125 mcg per day.

Compound (II) may for example be administered by inhalation at a dose of from about 1 mcg to about 400 mcg/day (calculated as the free base). In one embodiment Compound (II), and specifically 4-{(1R)-2-[(6-{2-[(2,6-dichlorobenzyl)oxy]ethoxy}hexyl)amino]-1-hydroxyethyl}-2-(hydroxymethyl)phenol triphenylacetate, may be administered by inhalation at a dose of from about 1 mcg to 100 mcg/day, for example 3, 6.25, 12.5, 25, 50 or 100 mcg/day (calculated as the free base). In general Compound (II) will be administered as a once-daily dose. In one embodiment Compound (II) may be administered by inhalation at a dose of 12.5 mcg/day. In another embodiment Compound (II) may be administered by inhalation at a dose of 25 mcg/day. In another embodiment Compound (II) may be administered by inhalation at a dose of 50 mcg/day.

In a further embodiment, 4-{(1R)-2-[(6-{2-[(2,6-dichlorobenzyl)oxy]ethoxy}hexyl)amino]-1-hydroxyethyl}-2-(hydroxymethyl)phenol triphenylacetate, may be administered by inhalation, once-daily, at a dose of 25 mcg per day.

In a further embodiment, the present invention provides a pharmaceutical combination product for once-daily administration by inhalation, comprising 4-{(1R)-2-[(6-{2-[(2,6-dichlorobenzyl)oxy]ethoxy}hexyl)amino]-1-hydroxyethyl}-2-(hydroxymethyl)phenol triphenylacetate at a dose of 25 mcg per day, and (4-[hydroxy(diphenyl)methyl]-1-{2-[(phenylmethyl)oxy]ethyl}-1-azoniabicyclo[2.2.2]octane bromide at a dose of 125 mcg per day.

In a further embodiment, the present invention provides a pharmaceutical combination product for once-daily administration by inhalation, comprising 4-{(1R)-2-[(6-{2-[(2,6-dichlorobenzyl)oxy]ethoxy}hexyl)amino]-1-hydroxyethyl}-2-(hydroxymethyl)phenol triphenylacetate at a dose of 25 mcg per day, and (4-[hydroxy(diphenyl)methyl]-1-{2-[(phenylmethyl)oxy]ethyl}-1-azoniabicyclo[2.2.2]octane bromide at a dose of 62.5 mcg per day.

When the combination additionally includes an inhaled corticosteroid, this may be used at doses compatible with those known for monotherapy. When the inhaled corticosteroid is fluticasone furoate this may be administered by inhalation at a dose of from about 25 mcg to about 800 mcg daily, and if necessary in divided doses. Thus, the daily dose of fluticasone furoate may be for example 25, 50, 100, 200, 300, 400, 600 or 800 mcg, in general as a once-daily dose. In one embodiment, the daily dose of fluticasone furoate is 100 mcg. In a further embodiment, the daily dose of fluticasone furoate is 50 mcg.

The individual compounds of the pharmaceutical combination product as described herein may be administered either sequentially or simultaneously in separate or combined pharmaceutical formulations/compositions. Thus Compound (I) and Compound (II) may for example, be formulated separately and presented in separate packs or devices, or said individually formulated components may be presented in a single pack or device. Where appropriate, the individual compounds may be admixed within the same formulation, and presented as a fixed pharmaceutical combination. In general such formulations will include pharmaceutical carriers or excipients as described hereinafter, but combinations of the compounds without any excipients are also within the ambit of this invention. In one embodiment, the individual compounds of the pharmaceutical combination product may be administered simultaneously in a combined pharmaceutical formulation or composition.

When the pharmaceutical combination product additionally includes an inhaled corticosteroid, eg 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate) this may likewise be formulated separately, either with or without one or more pharmaceutical carriers or excipients, and presented for either sequential or simultaneous administration, or the inhaled corticosteroid may be admixed with either Compound (I) and/or Compound (II). 6α,9α-Difluoro-17α-[(2-furanylcarbonyl)oxy]-11β-hydroxy-16α-methyl-3-oxo-androsta-1,4-diene-17β-carbothioic acid S-fluoromethyl ester may be formulated for example as described in WO02/12265, or as described hereinafter.

In further aspects the invention therefore provides:
A pharmaceutical combination product comprising Compound (I) and Compound (II) presented separately for sequential or simultaneous administration;
A pharmaceutical combination product comprising Compound (I) and Compound (II) presented separately but held in the same pack or device, for sequential or simultaneous administration; and
A pharmaceutical combination product comprising Compound (I) and Compound (II) in admixture with each other for simultaneous administration.

In each case, each of Compound (I) and/or Compound (II) may be formulated with or without pharmaceutical carriers or excipients.

The present invention further provides a pharmaceutical combination product comprising Compound (I) and Compound (II) wherein at least one of Compound (I) and Compound (II) is formulated with a pharmaceutically acceptable carrier or excipient.

The present invention further provides a pharmaceutical combination product comprising Compound (I) and Compound (II) wherein each of Compound (I) and Compound (II) is formulated with a pharmaceutically acceptable carrier or excipient.

In one embodiment of this invention compositions of Compounds (I) and (II) include those suitable for inhalation, including fine particle powders, or mists which may be generated and administered by means of various types of inhalers for example, reservoir dry powder inhalers, unit-dose dry powder inhalers, pre-metered multi-dose dry powder inhalers, nasal inhalers or pressurized metered dose inhalers, nebulisers or insufflators.

The compositions may be prepared by any of the methods well known in the art of pharmacy. In general, said methods include the step of bringing the active ingredient(s) into association with the carrier which constitutes one or more accessory ingredients. In general the compositions are prepared by uniformly and intimately bringing into association the active ingredient with liquid carriers or finely divided solid carriers or both and then, if necessary, shaping the product into the desired composition.

Powder compositions generally contain a powder mix for inhalation of the active ingredient and a suitable powder base (carrier/diluent/excipient substance) such as mono-, di or poly-saccharides (e.g. lactose or starch). Use of lactose is preferred. The lactose may be for example anhydrous lactose or α-lactose monohydrate. In one embodiment, the carrier is α-lactose monohydrate. Dry powder compositions may also include, in addition to the active ingredient and carrier, a further excipient (eg a ternary agent) such as a sugar ester, calcium stearate or magnesium stearate.

Alternatively, the active ingredient may be presented without excipients. For the avoidance of doubt use of the term 'composition' or 'formulation' herein refers to the active ingredients either with or without excipients or carriers.

The present invention further provides a pharmaceutical combination product comprising Compound (I) and Compound (II) wherein at least one of Compound (I) and Compound (II) is formulated with a pharmaceutically acceptable carrier and a ternary agent.

The present invention further provides a pharmaceutical combination product comprising Compound (I) and Compound (II) wherein Compound (II) is formulated with a pharmaceutically acceptable carrier and a ternary agent.

In another embodiment the present invention further provides a pharmaceutical formulation comprising a combination of Compound (I) and Compound (II) wherein both Compounds are formulated with a pharmaceutically acceptable carrier and a ternary agent.

The present invention further provides a pharmaceutical combination product for inhaled administration comprising 4-{(1R)-2-[(6-{2-[(2,6-dichlorobenzyl)oxy]ethoxy}hexyl) amino]-1-hydroxyethyl}-2-(hydroxymethyl)phenol triphenylacetate and (4-[hydroxy(diphenyl)methyl]-1-{2-[(phenylmethyl)oxy]ethyl}-1-azoniabicyclo[2.2.2]octane bromide each formulated separately with a pharmaceutically acceptable carrier and a ternary agent, but held in the same pack or device, for sequential or simultaneous administration.

In one embodiment said ternary agent is magnesium stearate.

The present invention further provides a pharmaceutical combination product for inhaled administration comprising 4-{(1R)-2-[(6-{2-[(2,6-dichlorobenzyl)oxy]ethoxy}hexyl) amino]-1-hydroxyethyl}-2-(hydroxymethyl)phenol triphenylacetate and (4-[hydroxy(diphenyl)methyl]-1-{2-[(phenylmethyl)oxy]ethyl}-1-azoniabicyclo[2.2.2]octane bromide each formulated separately with lactose, as a pharmaceutically acceptable carrier, and magnesium stearate, as a ternary agent, but held in the same pack or device, for sequential or simultaneous administration.

The compositions may be presented in unit dosage form. Dry powder compositions for topical delivery to the lung by inhalation may, for example, be presented in capsules and cartridges of for example gelatine, or blisters of for example laminated aluminium foil, for use in an inhaler or insufflator.

Each capsule, cartridge or blister may generally contain between 1 mcg-1000 mcg, e.g. 100 to 500 mcg of Compound (I) and/or between 1 mcg-400 mcg, e.g 1 to 100 mcg of Compound (II). Packaging of the formulation may be suitable for unit dose or multi-dose delivery. As indicated above Compound (I) and Compound (II) may be formulated independently or in admixture. Said compounds may thus be incorporated in separate unit doses or may be combined in a single unit dose with or without additional excipients as deemed necessary.

In a further embodiment, each capsule, cartridge or blister may contain 125 mcg or 62.5 mcg of Compound (I) and/or 25 mcg of Compound (II).

In yet a further embodiment, each capsule, cartridge or blister may contain 125 mcg or 62.5 mcg of (4-[hydroxy (diphenyl)methyl]-1-{2-[(phenylmethyl)oxy]ethyl}-1-azoniabicyclo[2.2.2]octane bromide and/or 25 mcg of 4-{(1R)-2-[(6-{2-[(2,6-dichlorobenzyl)oxy]ethoxy}hexyl)amino]-1-hydroxyethyl}-2-(hydroxymethyl)phenol triphenylacetate.

In one embodiment, a composition suitable for inhaled administration may be incorporated into a plurality of sealed dose containers provided on medicament pack(s) mounted inside a suitable inhalation device. The containers may be rupturable, peelable or otherwise openable one-at-a-time and the doses of the dry powder composition administered by inhalation on a mouthpiece of the inhalation device, as known in the art. The medicament pack may take a number of different forms, for instance a disk-shape or an elongate strip. Representative inhalation devices are the DISKHALER™ and DISKUS™ devices, marketed by GlaxoSmithKline. The DISKUS™ inhalation device is, for example, described in GB 2242134A.

A dry powder inhalable composition, may also be provided as a bulk reservoir in an inhalation device, the device then being provided with a metering mechanism for metering a dose of the composition from the reservoir to an inhalation channel where the metered dose is able to be inhaled by a patient inhaling at a mouthpiece of the device. Exemplary marketed devices of this type are TURBUHALER™ of AstraZeneca, TWISTHALER™ of Schering and CLICKHALER™ of Innovata.

A further delivery method for a dry powder inhalable composition is for metered doses of the composition to be provided in capsules (one dose per capsule) which are then loaded into an inhalation device, typically by the patient on demand. The device has means to rupture, pierce or otherwise open the capsule so that the dose is able to be entrained into the patient's lung when they inhale at the device mouthpiece. As marketed examples of such devices there may be mentioned ROTAHALER™ of GlaxoSmithKline and HANDIHALER™ of Boehringer Ingelheim.

A dry powder composition may also be presented in a delivery device which permits separate containment of Compound (I) and Compound (II) optionally in admixture with one or more excipients. Thus, for example, the individual compounds of the combination are administrable simultaneously but are stored separately, e.g. in separate pharmaceutical compositions, for example as described in WO 2003/061743 A1, WO 2007/012871 A1 and/or WO2007/068896. In one embodiment a delivery device permitting separate containment of actives is an inhaler device having two medicament packs in peelable blister strip form, each pack containing pre-metered doses in blister pockets arranged along its length. Said device has an internal indexing mechanism which, each time the device is actuated, peels opens a pocket of each strip and positions the packs so that each newly exposed dose of each pack is adjacent a manifold which communicates with a mouthpiece of the device. When the patient inhales at the mouthpiece, each dose is simultaneously drawn out of its associated pocket into the manifold and entrained via the mouthpiece into the patient's respiratory tract. Thus, each time the device is used, the patient is administered a combination therapy consisting of a dose from each medicament pack. A further device that permits separate containment of different compounds is DUOHALER™ of Innovata.

In a further embodiment, the present invention provides a dry powder inhaler (Inhaler 1) comprising two compositions presented separately, wherein a first composition comprises
  i. 4-[hydroxy(diphenyl)methyl]-1-{2-[(phenylmethyl)oxy]ethyl}-1-azoniabicyclo[2.2.2]octane bromide, and
  ii. lactose, and
  iii. magnesium stearate at an amount of about 0.6% w/w based on the total weight of the first composition;
and a second composition comprises
  i. 4-{(1R)-2-[(6-{2-[(2,6-dichlorobenzyl)oxy]ethoxy}hexyl)amino]-1-hydroxyethyl}-2-(hydroxymethyl)phenol triphenylacetate, and
  ii. lactose, and
  iii. magnesium stearate at an amount of about 1.0% w/w based on the total weight of the second composition.

In a further embodiment, the present invention provides Inhaler 1 wherein each composition is in unit dose form.

In a further embodiment, the present invention provides Inhaler 1 wherein the unit dose form is a capsule, cartridge or blister.

In a further embodiment, the present invention provides Inhaler 1 wherein 4-[hydroxy(diphenyl)methyl]-1-{2-[(phenylmethyl)oxy]ethyl}-1-azoniabicyclo[2.2.2]octane bromide is present in an amount of about 125 mcg/dose.

In a further embodiment, the present invention provides Inhaler 1 wherein 4-{(1R)-2-[(6-{2-[(2,6-dichlorobenzyl)oxy]ethoxy}hexyl)amino]-1-hydroxyethyl}-2-(hydroxymethyl)phenol triphenylacetate is present in an amount of about 25 mcg/dose.

In a further embodiment, the present invention provides Inhaler 1 wherein the second composition further comprises 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate).

In a further embodiment, the present invention provides Inhaler 1 wherein 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate) is present in an amount of about 100 mcg/dose.

Spray compositions for inhalation may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain the pharmaceutical product and a suitable propellant such as a fluorocarbon or hydrogen-containing chlorofluorocarbon or mixtures thereof, particularly hydrofluoroalkanes, especially 1,1,1,2-tetrafluoroethane, 1,1,1,2,3,3,3-heptafluoro-n-propane or a mixture thereof. The aerosol composition may optionally contain additional formulation excipients well known in the art such as surfactants e.g. oleic acid, lecithin or an oligolactic acid derivative e.g. as described in WO94/21229 and WO98/34596 and/or cosolvents e.g. ethanol. Pressurised formulations will generally be retained in a canister (e.g. an aluminium canister) closed with a valve (e.g. a metering valve) and fitted into an actuator provided with a mouthpiece.

There is thus provided as a further aspect of the invention a pharmaceutical combination product comprising Compound (I) and Compound (II) formulated individually or in admixture, with a fluorocarbon or hydrogen-containing chlorofluorocarbon as propellant, optionally in combination with a surface-active agent and/or a co-solvent. According to another aspect of the invention, the propellant is selected from 1,1,1,2-tetrafluoroethane, 1,1,1,2,3,3,3-heptafluoro-n-propane and mixtures thereof.

Another aspect of the invention is a pharmaceutical combination product consisting of Compound (I) and Compound (II) formulated individually or in admixture, with a fluorocarbon or hydrogen-containing chlorofluorocarbon as propellant, optionally in combination with a surface-active agent and/or a cosolvent. In another embodiment of the invention the propellant is selected from 1,1,1,2-tetrafluoroethane, or 1,1,1,2,3,3,3-heptafluoro-n-propane and mixtures thereof.

Where appropriate compositions according to the invention may be buffered by the addition of suitable buffering agents.

Active ingredients for administration by inhalation desirably have a controlled particle size. The optimum particle size for inhalation into the bronchial system is usually 1-10 μm, preferably 2-5 μm. Particles having a size above 20 μm are generally too large when inhaled to reach the small airways. To achieve these particle sizes the particles of the active ingredient as produced may be size reduced by conventional means e.g. by micronization. The desired fraction may be separated out by air classification or sieving. Preferably, the particles will be crystalline.

Dry powder compositions according to the invention may comprise a carrier. The carrier when it is lactose e.g. α-lactose monohydrate, may form from about 91 to about 99%, e.g. 97.7-99.0% or 91.0-99.2% by weight of the formulation. In general, the particle size of the carrier, for example lactose, will be much greater than the inhaled medicament within the present invention. When the carrier is lactose it will typically be present as milled lactose, having a MMD (mass median diameter) of 60-90 μm.

The lactose component may comprise a fine lactose fraction. The 'fine' lactose fraction is defined as the fraction of lactose having a particle size of less than 7 μm, such as less than 6 μm, for example less than 5 μm. The particle size of the 'fine' lactose fraction may be less than 4.5 μm. The fine lactose fraction, if present, may comprise 2 to 10% by weight of the total lactose component, such as 3 to 6% by weight fine lactose, for example 4.5% by weight fine lactose.

Magnesium stearate, if present in the composition, is generally used in an amount of about 0.2 to 2%, e.g. 0.6 to 2% or 0.5 to 1.75%, e.g. 0.6%, 0.75%, 1%, 1.25% or 1.5% w/w, based on the total weight of the composition. The magnesium stearate will typically have a particle size in the range 1 to 50 μm, and more particularly 1-20 μm, e.g. 1-10 μm. Commercial sources of magnesium stearate include Peter Greven, Covidien/Mallinckodt and FACI.

In a further embodiment there is provided a pharmaceutical combination product comprising Compound (I) and Compound (II) wherein Compound (I) is (4-[hydroxy(diphenyl)methyl]-1-{2-[(phenylmethyl)oxy]ethyl}-1-azoniabicyclo[2.2.2]octane bromide and is presented as a dry powder composition containing magnesium stearate at an amount of 0.6% w/w based on the total weight of the composition.

In yet a further embodiment, there is provided a pharmaceutical combination product comprising Compound (I) and Compound (II) wherein Compound (II) is 4-{(1R)-2-[(6-{2-[(2,6-dichlorobenzyl)oxy]ethoxy}hexyl)amino]-1-hydroxyethyl}-2-(hydroxymethyl)phenol triphenylacetate and is presented as a dry powder composition containing magnesium stearate at an amount of 1.0% w/w based on the total weight of the composition.

Intranasal sprays may be formulated with aqueous or non-aqueous vehicles with the addition of agents such as thickening agents, buffer salts or acid or alkali to adjust the pH, isotonicity adjusting agents or anti-oxidants.

Solutions for inhalation by nebulization may be formulated with an aqueous vehicle with the addition of agents such as acid or alkali, buffer salts, isotonicity adjusting agents or antimicrobials. They may be sterilized by filtration or heating in an autoclave, or presented as a non-sterile product.

The invention also provides a method of preparing a pharmaceutical combination product as defined herein, the method comprising either:

(a) preparing a separate pharmaceutical composition for administration of the individual compounds of the combination either sequentially or simultaneously, or (b) preparing a combined pharmaceutical composition for administration of the individual compounds together in the combination for simultaneous use, wherein the pharmaceutical composition comprises the combination together with one or more pharmaceutically acceptable carriers and/or excipients.

4-{(1R)-2-[(6-{2-[(2,6-dichlorobenzyl)oxy]ethoxy}hexyl)amino]-1-hydroxyethyl}-2-(hydroxymethyl)phenol, and its salts, including 4-{(1R)-2-[(6-{2-[(2,6-dichlorobenzyl)oxy]ethoxy}hexyl)amino]-1-hydroxyethyl}-2-(hydroxymethyl)phenol triphenylacetate may be prepared as described in WO03/024439 (Example 78(i)), which is incorporated by reference herein.

4-[hydroxy(diphenyl)methyl]-1-{2-[(phenylmethyl)oxy]ethyl}-1-azoniabicyclo[2.2.2]octane bromide is described as Example 84, in WO2005/104745 which is incorporated by reference herein.

Clinical Studies

4-[hydroxy(diphenyl)methyl]-1-{2-[(phenylmethyl)oxy]ethyl}-1-azoniabicyclo[2.2.2]octane bromide 4-[hydroxy(diphenyl)methyl]-1-{2-[(phenylmethyl)oxy]ethyl}-1-azoniabicyclo[2.2.2]octane bromide has been found to be an effective long-acting potent, pan-active anti-muscarinic bronchodilator which demonstrates slow reversibility at the human M3 receptor in vitro and long duration of action in vivo when administered directly to the lungs in pre-clinical models. The long duration of action of this compound identified using in vitro models, when administered via inhalation in animals, and subsequently in early phase studies in healthy volunteers and COPD subjects supports the potential for use of this compound as a once daily bronchodilator for COPD.

Several clinical pharmacology studies have been conducted using 4-[hydroxy(diphenyl)methyl]-1-{2-[(phenylmethyl)oxy]ethyl}-1-azoniabicyclo[2.2.2]octane bromide in both healthy volunteers and COPD patients to investigate the safety, tolerability, pharmacokinetics and pharmacodynamics of this compound. The bronchodilatory effects and duration of action of single inhaled doses of this compound as measured by plethysmography ($sG_{aw}$, $R_{aw}$) and spirometry ($FEV_1$) were assessed in some of the above noted studies. These studies showed clinically relevant bronchodilation and 24 h duration of action for the compound.

In one such study, designed to evaluate the safety, efficacy and pharmacokinetics of 4-[hydroxy(diphenyl)methyl]-1-{2-[(phenylmethyl)oxy]ethyl}-1-azoniabicyclo[2.2.2]octane bromide in subjects with COPD, five once-daily doses (62.5 mcg, 125 mcg, 250 mcg, 500 mcg and 1000 mcg), taken over a 14-day treatment period, produced statistically significant improvements in pulmonary function compared to placebo. All once-daily doses showed numerically greater improvement in trough $FEV_1$ than the open label tiotropium active control (18 mcg once-daily). In addition, this study confirmed that 4-[hydroxy(diphenyl)methyl]-1-{2-[(phenylmethyl)oxy]ethyl}-1-azoniabicyclo[2.2.2]octane bromide has a once-daily profile.

A further study evaluated the efficacy and safety of three doses (125 mcg, 250 mcg and 500 mcg) of 4-[hydroxy(diphenyl)methyl]-1-{2-[(phenylmethyl)oxy]ethyl}-1-azoniabicyclo[2.2.2]octane bromide administered once-daily via a dry powder inhaler over a 28 day period in subjects with COPD. This study confirmed that 4-[hydroxy(diphenyl)methyl]-1-{2-[(phenylmethyl)oxy]ethyl}-1-azoniabicyclo[2.2.2]octane bromide appears to be safe and efficacious, maintaining significant bronchodilation over twenty four hours.

Compound (II) (as the α-Phenylcinnamate Salt or the Triphenylacetate Salt)

Compound (II) as the α-phenylcinnamate salt and the triphenylacetate salt has been studied in a number of clinical pharmacology studies, including single- and repeat-dose studies. In addition, these studies have evaluated Compound (II) formulated with lactose and either cellobiose octaacetate or magnesium stearate.

In asthmatic patients, a statistically and clinically significant improvement in trough (24-hour) FEV1 was observed for all doses of Compound (II) tested, compared to placebo. Single doses of 25 μg to 100 μg of Compound (II) triphenylacetate (containing lactose and magnesium stearate) demonstrated 24 hour duration of action as assessed by a 200 mL or greater increase in mean 23 to 24 hour post-dose FEV1 versus placebo.

In COPD patients, treatment with 100 mcg and 400 mcg Compound (II) alpha-phenylcinnamate (with lactose alone) achieved a clinically relevant adjusted mean difference from placebo in weighted mean trough $FEV_1$ (22 to 24 hrs) of >100 mL. Single doses of 25 μg to 100 μg of Compound (II) triphenylacetate (containing lactose and magnesium stearate) demonstrated 24 hour duration of action as assessed by a 190 mL or greater increase in mean 23 to 24 hour post-dose FEV1 versus placebo).

Combination Therapy

A combination of Compound (I) bromide and Compound (II) triphenylacetate has been administered to sixteen healthy Japanese volunteers, aged 20 to 65, as part of a clinical trial to assess the safety, tolerability, pharmacokinetics and pharmacodynamics of single inhaled doses of Compound (I) bromide and Compound (II) triphenylacetate as monotherapies and in combination. This study was a randomised, double blind, placebo-controlled, four-way crossover study wherein subjects received a single dose of:

Compound (I) bromide (500 mcg dose),
Compound (II) triphenylacetate (50 mcg dose),
Compound (I) bromide (500 mcg dose) and Compound (II) triphenylacetate (50 mcg dose) concurrently, or
placebo at each of the four treatment periods. On enrolment into the study subjects were assigned to one of four treatment sequences based on a Williams design.

This clinical study in healthy Japanese volunteers, evaluated the effect of Compound (I) bromide (500 mcg dose) and Compound (II) triphenylacetate (50 mcg dose) administered as single inhaled doses and concurrently (Compound (I) bromide (500 mcg dose) and Compound (II) triphenylacetate (50 mcg dose)) on lung function parameters. Single inhaled doses and the combination administered using dry powder inhalers were found to be well tolerated. In this study $FEV_1$ values were recorded. $FEV_1$ values were higher for all treatment groups compared with placebo. The group dosed with Compound (I) bromide (500 mcg dose) and Compound (II) triphenylacetate (50 mcg dose) concurrently showing the largest difference relative to placebo.

Pharmaceutical Formulations
Preparation of Blends
Compound (I) Bromide

Pharmaceutical grade α-lactose monohydrate, sourced from DMV Fronterra Excipients, complying with the requirements of Ph.Eur/USNF may be used. Before use, the α-lactose monohydrate may be sieved through a coarse screen (for example with a mesh size 500 or 800 microns). The level of fines in the α-lactose monohydrate, which can be measured by Sympatec, may be 4.5% w/w less than 4.5 micron.

Compound (I) bromide is micronised before use in an APTM microniser to give a mass median diameter of 1 to 5 microns, such as 2 to 5 microns.

Pharmaceutical grade magnesium stearate, sourced from Peter Greven, complying with the requirements of Ph.Eur/USNF may be used as supplied with a mass median particle size of 8 to 12 microns.

Blend A

Lactose monohydrate may be passed through a sieve and then combined with magnesium stearate and blended using either a high shear mixer (a QMM, PMA or TRV series mixer, such as TRV25 or TRV65) or a low shear tumbling blender (a Turbula mixer) to provide a magnesium stearate/lactose premix, hereinafter referred to as blend A.

Blend B

Final blend B may be obtained as follows. An quantity of blend A and compound (I) bromide may be screened, for example using a COMIL™, and then blended with the remaining blend A using either a high shear mixer (a QMM, PMA or TRV series mixer, such as TRV25 or TRV65) or a low shear tumbling blender (a Turbula mixer).

| Representative Batch Formula for Compound (I) Bromide Powder Blend (62.5 microgram per blister) | |
|---|---|
| Ingredient | Quantity |
| Micronised Compound (I) Bromide | 74.1 g |
| Magnesium Stearate | 75 g |
| Lactose Monohydrate | To 12.5 kg |

Note:
74.1 g of Compound (I) Bromide is equivalent to 62.5 g of the free cation. The quantity of Compound (I) Bromide added may be adjusted to reflect the assigned purity of the input drug substance.

| Representative Batch Formula for Compound (I) Bromide Powder Blend (125 microgram per blister) | |
|---|---|
| Ingredient | Quantity |
| Micronised Compound (I) Bromide | 148.3 g |
| Magnesium Stearate | 75 g |
| Lactose Monohydrate | To 12.5 kg |

Note:
148.3 g of Compound (I) Bromide is equivalent to 125 g of the free cation. The quantity of Compound (I) Bromide added may be adjusted to reflect the assigned purity of the input drug substance.

| Blending Parameters (using a TRV25, 12.5 kg scale) | | |
|---|---|---|
| Blend | Time (mins) | Approximate Speed (rpm) |
| A | 6 | 460 |
| B | 10 | 590 |

Blister Strip Preparation

The blended composition may then be transferred into blister strips (typical nominal mean quantity of blend per blister is 12.5-13.5 mg) of the type generally used for the supply of dry powder for inhalation and the blister strips were sealed in the customary fashion.

Compound (II) Triphenylacetate

Pharmaceutical grade α-lactose monohydrate, which can be sourced from DMV Fronterra Excipients, complying with the requirements of Ph.Eur/USNF may be used. Before use, the α-lactose monohydrate may be sieved through a coarse screen (typical mesh size 500 microns). The level of fines in the α-lactose monohydrate, which can be measured by Sympatec, may be 4.5% w/w less than 4.5 micron.

Compound (II) triphenylacetate is micronised before use in an APTM microniser to give a MMD (mass median diameter) of from 1 to 5 microns, such as 2 to 5 microns, for example 1.8 microns.

Pharmaceutical grade Magnesium stearate, which can be sourced from Peter Greven, complying with the requirements of Ph.Eur/USNF may be used as supplied with a mass median particle size 8 to 12 microns.

Blend A

Lactose monohydrate may be passed through a sieve and then combined with magnesium stearate (typically 130 g) and blended using either a high shear mixer (a QMM, PMA or TRV series mixer, such as TRV25 or TRV65) or a low shear tumbling blender (a Turbula mixer) to provide a magnesium stearate/lactose premix, hereinafter referred to as blend A.

Blend B

Final blend B may be obtained as follows. An appropriate quantity of blend A and compound (II) triphenylacetate (typically 5-165 g) may be screened, for example using a COMIL™, and then blended with the remaining blend A using either a high shear mixer (a QMM, PMA or TRV series mixer) or a low shear tumbling blender (a Turbula mixer). The final concentration of compound (II) triphenylacetate in the blends is typically in the range 0.02% w/w-0.8% w/w free base equivalent.

Blister Strip Preparation

The blended composition is transferred into blister strips (typical nominal mean quantity of blend B per blister is 12.5-13.5 mg) or the type generally used for the supply of dry powder for inhalation and the blister strips are then sealed in the customary fashion.

Example Preparations

Using the above-described procedure the following exemplary formulations may be prepared:

| Blend No | Mass of Magnesium stearate | Mass of compound (II) triphenylacetate (micronised) | Mass of lactose | Quantity per blister |
|---|---|---|---|---|
| 1 | 130 g | 5.0 g | To 13 kg | 13 mg |
| 2 | 130 g | 10.3 g | To 13 kg | 13 mg |
| 3 | 130 g | 20.7 g | To 13 kg | 13 mg |
| 4 | 130 g | 41.3 g | To 13 kg | 13 mg |

-continued

| Blend No | Mass of Magnesium stearate | Mass of compound (II) triphenylacetate (micronised) | Mass of lactose | Quantity per blister |
|---|---|---|---|---|
| 5 | 130 g | 82.7 g | To 13 kg | 13 mg |
| 6 | 130 g | 165.4 g | To 13 kg | 13 mg |

Note:
The quantity of compound (II) triphenylacetate used is based on a base to salt conversion factor of 1.59. For example, 41 g of Compound (II) triphenylacetate is equivalent to 25 g of the free base.

Example Blending Parameters (using a TRV25, 13 kg scale, Compound (II) triphenylacetate powder blend (25 microgram blister))

| Blend | Time (mins) | Approximate Speed (rpm) |
|---|---|---|
| A | 9 | 550 |
| B | 8.5 | 550 |

Example Dry Powder Inhaler Devices

Compound (I) bromide and Compound (II) triphenylacetate as an inhalation powder may be administered in a DPI device containing two blister strips. One strip contains a blend of micronised Compound (I) bromide (approximately 500 micrograms per blister), magnesium stearate and lactose monohydrate. The second strip contains a blend of micronised Compound (II) triphenylacetate (approximately 25 micrograms per blister), magnesium stearate and lactose monohydrate. The DPI device will deliver, when actuated, the contents of a single blister simultaneously from each of the two blister strips. Each blister strip is a double foil laminate containing 30 blisters per strip.

In a further embodiment, Compound (I) bromide and Compound (II) triphenylacetate as an inhalation powder may be administered in a dry powder inhaler device containing two blister strips, wherein one strip contains a blend of micronised Compound (I) bromide (approximately 125 or 62.5 micrograms per blister), magnesium stearate (at an amount of 0.6% w/w of the total powder weight per blister) and lactose monohydrate. The second strip contains a blend of micronised Compound (II) triphenylacetate (approximately 25 micrograms per blister), magnesium stearate and lactose monohydrate. The second strip optionally further comprises 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate) at an amount of approximately 100 micrograms per blister. The DPI device will deliver, when actuated, the contents of a single blister simultaneously from each of the two blister strips. Each blister strip is a double foil laminate containing 7, 14 or 30 filled blisters per strip.

In a further embodiment, Compound (I) bromide and Compound (II) triphenylacetate as an inhalation powder may be administered in a dry powder inhaler device containing two blister strips, wherein one strip contains a blend of micronised Compound (I) bromide (approximately 125 or 62.5 micrograms per blister), Compound (II) triphenylacetate (approximately 25 micrograms per blister), magnesium stearate and lactose monohydrate. The second strip contains a blend of 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate) at an amount of approximately 100 micrograms per blister, and lactose monohydrate. The DPI device will deliver, when actuated, the contents of a single blister simultaneously from each of the two blister strips. Each blister strip is a double foil laminate containing 7, 14 or 30 filled blisters per strip.

"Thus the present application describes, for example:

1. A pharmaceutical combination product comprising
a) a compound of the formula:

Compound (I)

wherein
X$^-$ is a pharmaceutically acceptable anion; and
  b) a compound of the formula:

or a pharmaceutically acceptable salt thereof (Compound (II)).

2. A product according to claim 1 wherein for Compound (I) the pharmaceutically acceptable anion is selected from the group consisting of chloride, bromide, iodide, hydroxide, sulfate, nitrate, phosphate, acetate, trifluoroacetate, fumarate, citrate, tartrate, oxalate, succinate, mandelate, methanesulfonate or p-toluenesulfonate.

3. A product according to claim 1 or claim 2 wherein Compound (I) is 4-[hydroxy(diphenyl)methyl]-1-{2-[(phenylmethyl)oxy]ethyl}-1-azoniabicyclo[2.2.2]octane bromide.

4. A product according to any of claims 1 to 3 wherein Compound (II) is 4-{(1R)-2-[(6-{2-[(2,6-dichlorobenzyl)oxy]ethoxy}hexyl)amino]-1-hydroxyethyl}-2-(hydroxymethyl) phenol α-phenylcinnamate.

5. A product according to any of claims 1 to 3 wherein Compound (II) is 4-{(1R)-2-[(6-{2-[(2,6-dichlorobenzyl)oxy]ethoxy}hexyl)amino]-1-hydroxyethyl}-2-(hydroxymethyl) phenol triphenylacetate 6. A product according to any of claims 1 to 5 wherein Compound (I) and Compound (II) are presented in a form adapted for separate administration.

7. A product according to any of claims 1 to 5 wherein Compound (I) and Compound (II) are presented in a form adapted for sequential administration.

8. A product according to any of claims 1 to 5 wherein Compound (I) and Compound (II) are presented in a form adapted for simultaneous administration.

9. A product according to claim 8 wherein Compound (I) and Compound (II) are in admixture with each other.

10. A product according to any of claims 1 to 9 wherein at least one of Compound (I) and Compound (II) is formulated with a pharmaceutically acceptable carrier or excipient.

11. A product according to any of claims 1 to 9 in a form suitable for administration by oral or nasal inhalation.

12. A product according to claim 11 wherein the form is suitable for administration by inhalation via a medicament dispenser selected from a reservoir dry powder inhaler, a unit-dose dry powder inhaler, a pre-metered multi-dose dry powder inhaler, a nasal inhaler or a pressurized metered dose inhaler.

13. A product as claimed in claim 12 wherein each of Compound (I) and Compound (II) is presented in the form of a dry powder composition.

14. A product as claimed in claim 13 wherein Compound (I) and Compound (II) are presented as separate compositions.

15. A product as claimed in claim 13 wherein Compound (I) and Compound (II) are presented as admixed compositions.

16. A product as claimed in claim 14 or 15 wherein at least one of said compositions of Compound (I) or Compound (II) contains a carrier.

17. A product as claimed in claim 14 or 15 wherein both compositions of Compound (I) and Compound (II) contain a carrier.

18. A product as claimed in claim 16 or 17 wherein the carrier is lactose.

19. A product as claimed in any of claims 13 to 18 wherein at least one of said compositions contains a ternary agent.

20. A product as claimed in any of claims 13 to 18 wherein both compositions contain a ternary agent.

21. A product as claimed in claim 19 wherein the ternary agent is magnesium stearate.

22. A product as claimed in claim 20, wherein the ternary agent in both compositions is magnesium stearate.

23. A product as claimed in claim 22, wherein magnesium stearate is present in an amount of about 0.6%w/w in a composition of Compound (I), and/or an amount of about 1.0%w/w in a composition of Compound (II).

24. A product as claimed in any one of claims 13 to 23 wherein said separate or admixed compositions are in unit dose form.

25. A product as claimed in claim 24 wherein the unit dose form is in a capsule, cartridge or blister pack.

26. A product as claimed in any of claims 13 to 25 wherein the composition is administered via a dry powder inhaler.

27. A product as claimed in claim 26 wherein said inhaler permits separate containment of the active ingredients.

28. A product as claimed in any one of claims 1 to 27 wherein Compound (I) is present in an amount of about 1 to 1000 mcg/dose.

29. A product as claimed in any one of claims 1 to 27 wherein Compound (I) is present in an amount of 125mcg/dose.

30. A product as claimed in any one of claims 1 to 27 wherein Compound (I) is present in an amount of 62.5mcg/dose.

31. A product according to any one of claims 1 to 30 wherein Compound (II) is present in an amount of 1 to 100 mcg/dose.

32. A product according to any one of claims 1 to 30 wherein Compound (II) is present in an amount of 25mcg/dose.

33. A dry powder inhaler containing a product as defined in any of claims 1 to 32.

34. A product according to claim 11 wherein each of Compound (I) and Compound (II) is presented in the form of a spray composition for inhalation.

35. A product according to claim 34 wherein Compound (I) and Compound (II) are presented as separate or admixed compositions.

36. A product according to claim 34 or claim 35 wherein the spray composition is an aqueous solution or suspension.

37. A product according to claim 34 or 35 wherein the spray composition is an aerosol composition.

38. A product according to claim 37 comprising as propellant a fluorocarbon or hydrogen-containing chlorofluorocarbon.

39. A product according to claim 38 wherein the propellant is a hydrofluoroalkane.

40. A product according to claim 39 wherein the propellant is 1,1,1,2-tetrafluoroethane, 1,1,1,2,3,3,3-heptafluoro-n-propane or a mixture thereof. 41. A product according to any of claims 34 to 40 further comprising a co-solvent.

42. A product according to any of claims 34 to 41 further comprising a surface-active agent.

43. A product according to any of claims 1 to 42 further comprising an inhaled corticosteroid selected from the group consisting of fluticasone propionate, mometasone furoate, budesonide and 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate).

44. A product according to claim 43 wherein the inhaled corticosteroid is 6α,9α-difluoro-17α-[(2-furanylcarbonyl)oxy]-11β-hydroxy -16α-methyl-3-oxo-androsta-1,4-diene-17β-carbothioic acid S-fluoromethyl ester (fluticasone furoate).

45. A product according to claim 44, wherein or 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate) is present in an amount of 100mcg/dose.

46. A pressurised metered dose inhaler containing a product as defined in any of claims 1 to 11 and 34 to 45.

47. Use of the product as defined in any of claims 1 to 32 and 34 to 45 in the manufacture of a medicament for the prophylaxis or treatment of conditions for which administration of one or more of Compound (I) and Compound (II) is indicated.

48. The use according to claim 47, for the treatment of inflammatory or respiratory tract diseases, by simultaneous or sequential administration, in any order, of Compound (I) and Compound (II).

49. The use according to claim 47 or 48, for the manufacture of a medicament for the treatment of chronic obstructive pulmonary disease (COPD) and/or asthma by simultaneous or sequential administration of Compound (I) and Compound (II).

50. A method for the prophylaxis or treatment of inflammatory or respiratory tract diseases, comprising administering to a patient in need thereof, a product as defined in to any of claims 1 to 32 and 34 to 45.

51. A method according to claim 50 wherein the active ingredients of said product are administered either sequentially or simultaneously.

52. A method according to claim 50 or 51 wherein the disease is selected from the group consisting of chronic obstructive lung disease, chronic bronchitis, asthma, chronic respiratory obstruction, pulmonary fibrosis, pulmonary emphysema, allergic rhinitis, small airways disease, bronchiectasis and cystic fibrosis.

53. A method according to claim 52 wherein the disease is chronic obstructive lung disease (COPD).

54. A method according to claim 53 for the treatment of chronic obstructive pulmonary disease (COPD), by simultaneous or sequential administration of the active ingredients of a product as defined in any of claims 1 to 32 and 34 to 45.

55. A method according to any of claims 50 to 54 wherein administration is via inhalation by the mouth or nose.

56. A method according to claim 55 wherein administration is via a medicament dispenser selected from a reservoir dry powder inhaler, a pre-metered multi-dose dry powder inhaler, a nasal inhaler or a pressurized metered dose inhaler.

57. The method according to any of claims 50 to 56 wherein the product is administered once per day.

58. A product as defined in any of claims 1 to 32 and 34 to 45 for use in the treatment of inflammatory or respiratory tract diseases, by simultaneous or sequential administration, in any order, of Compound (I) and Compound (II).

59. A product according to claim 58 for use in the treatment of chronic obstructive pulmonary disease (COPD) and/or asthma by simultaneous or successive administration of Compound (I) and Compound (II).

60. A dry powder inhaler comprising two compositions presented separately, wherein the first composition comprises
   i. 4-[hydroxy(diphenyl)methyl]-1-{2-[(phenylmethyl)oxy]ethyl}-1-azoniabicyclo[2.2.2]octane bromide, and
   ii. lactose, and
   iii. magnesium stearate at an amount of about 0.6%w/w based on the total weight of the first composition;
and the second composition comprises
   i. 4-{(1R)-2-[(6-{2-[(2,6-dichlorobenzyl)oxy]ethoxy}hexyl)amino]-1-hydroxyethyl}-2-(hydroxymethyl)phenol Triphenylacetate, and
   ii. lactose, and
   iii. magnesium stearate at an amount of about 1.0%w/w based on the total weight of the second composition.

61. A dry powder inhaler according to claim 60, wherein each composition is in unit dose form.

62. A dry powder inhaler according to claim 61, wherein the unit dose form is a capsule, cartridge or blister.

63. A dry powder inhaler according to claim 61 or 62 wherein 4-[hydroxy(diphenyl) methyl]-1-{2-[(phenylmethyl)oxy]ethyl}-1-azoniabicyclo[2.2.2]octane bromide. is present in an amount of about 125mcg/dose.

64. A dry powder inhaler according to claim 61 or 62 wherein 4-[hydroxy (diphenyl)methyl]-1-{2-[(phenylmethyl)oxy]ethyl}-1-azoniabicyclo[2.2.2]octane bromide is present in an amount of about 62. 5mcg/dose.

65. A dry powder inhaler according to any of claims 61 to 64 wherein 4-{(1R)-2-[(6-{2-[(2,6-dichlorobenzyl)oxy]ethoxy}hexyl)amino]-1-hydroxyethyl}-2-(hydroxymethyl)phenol triphenylacetate is present in an amount of about 25mcg/dose.

66. A dry powder inhaler according to claim 60 wherein the second composition further comprises 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate).

67. A dry powder inhaler according to claims 61 to 65 wherein the second composition further comprises 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate).

68. A dry powder inhaler according to claim 67 wherein 6a,9a-difluoro-17a-[(2-furanylcarbonyl)oxy]-11P-hydroxy-16a-methyl-3-oxo-androsta-1,4-diene-17βcarbothioic acid S-fluoromethyl ester (fluticasone furoate) is present in an amount of about 100mcg/dose.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore, the Examples herein are to be construed as merely illustrative and not a limitation of the scope of the present invention in any way. The embodiments of the invention in which an exclusive property or privilege is claimed are defined as follows.

The invention claimed is:

1. A pharmaceutical combination product comprising:
   a) 4-[hydroxy(diphenyl)methyl]-1-{2-[(phenylmethyl)oxy]ethyl}-1-azoniabicyclo[2.2.2]octane bromide in an amount of about 62.5 mcg/dose, in the form of a dry powder; and
   b) 4-{(1R)-2-[(6-{2-[(2,6-dichlorobenzyl)oxy]ethoxy}hexyl)amino]-1-hydroxyethyl}-2-(hydroxymethyl)phenol triphenylacetate, in an amount of about 25 mcg/dose, in the form of a dry powder,
   wherein said pharmaceutical combination product is suitable for once-daily administration, and compounds a) and b) are presented in a form adapted for simultaneous administration.

2. The product according to claim 1, in a dry powder composition form suitable for administration by inhalation via a medicament dispenser, selected from the group consisting of a reservoir dry powder inhaler, a unit-dose dry powder inhaler, and a pre-metered multi-dose dry powder inhaler.

3. The product according to claim 2, wherein 4-[hydroxy(diphenyl)methyl]-1-{2-[(phenylmethyl)oxy]ethyl}-1-azoniabicyclo[2.2.2]octane bromide and 4-{(1R)-2-[(6-{2-[(2,6-dichlorobenzyl)oxy]ethoxy}hexyl)amino]-1-hydroxyethyl}-2-(hydroxymethyl)phenol triphenylacetate are separate dry powder compositions or admixed as a single dry powder composition.

4. The product according to claim 3, further comprising a carrier which comprises lactose.

5. The product according to claim 3, further comprising a ternary agent.

6. The product according to claim 5, further comprising a carrier; and wherein the ternary agent comprises magnesium stearate, wherein said magnesium stearate is present in an amount of about 0.6% w/w in the composition of 4-[hydroxy(diphenyl)methyl]-1-{2-[(phenylmethyl)oxy]ethyl}-1-azoniabicyclo[2.2.2]octane bromide, and/or an amount of about 1.0% w/w in a composition of 4-{(1R)-2-[(6-{2-[(2,6-dichlorobenzyl)oxy]ethoxy}hexyl)amino]-1-hydroxyethyl}-2-(hydroxymethyl)phenol triphenylacetate.

7. The product according to claim 3, wherein said separate compositions are in unit dose form selected from the group consisting of a capsule, a cartridge or a blister.

8. The product according to claim 1, further comprising 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate).

9. The product according to claim 8, wherein 6α,9αdifluoro-17α-[(2-furanylcarbonyl)oxy]-11β-hydroxy-16α-methyl-3-oxo-androsta-1,4-diene-17β-carbothioic acid S-fluoromethyl ester (fluticasone furoate) is present in an amount of about 100 mcg/dose.

10. A pharmaceutical combination product comprising:
 a) a first dry powder composition comprising 4-[hydroxy(diphenyl)methyl]-1-{2-[(phenylmethyl)oxy]ethyl}-1-azoniabicyclo[2.2.2]octane bromide, in an amount of about 62.5 mcg/dose; lactose; and magnesium stearate in an amount of about 0.6% w/w of said first dry powder composition; and
 b) a second dry powder composition comprising 4-{(1R)-2-[(6-{2-[(2,6-dichlorobenzyl)oxy]ethoxy}hexyl)amino]-1-hydroxyethyl}-2-(hydroxymethyl)phenol triphenylacetate, in an amount of about 25 mcg/dose; lactose, and; magnesium stearate in an amount of about 1.0% w/w of said second dry powder composition;
 wherein said pharmaceutical combination product is suitable for once-daily administration, and
 wherein the first and second dry powder compositions are configured for simultaneous administration.

11. The product according to claim 10, wherein the first and second dry powder compositions are presented in a form suitable for administration by inhalation via a medicament dispenser, said medicament dispenser being selected from the group consisting of a reservoir dry powder inhaler, a unit-dose dry powder inhaler, and a pre-metered multi-dose dry powder inhaler.

12. A pharmaceutical combination product comprising:
 a) 4-[hydroxy(diphenyl)methyl]-1-{2-[(phenylmethyl)oxy]ethyl}-1-azoniabicyclo[2.2.2]octane bromide in an amount of 62.5 mcg/dose, in the form of a dry powder;
 b) 4-{(1R)-2-[(6-{2-[(2,6-dichlorobenzyl)oxy]ethoxy}hexyl)amino]-1-hydroxyethyl}-2-(hydroxymethyl)phenol triphenylacetate, in an amount of 25 mcg/dose, in the form of a dry powder,
 c) 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate), in an amount of 100 mcg/dose, in the form of a dry powder,
 d) carrier excipient, and
 e) ternary agent, wherein said pharmaceutical combination product is suitable for once-daily administration, and compounds a), b) and c) are presented in a form adapted for simultaneous administration.

13. The pharmaceutical combination product of claim 12, wherein:
 a first dry powder composition comprises an admixture of compound a), compound b), carrier excipient d), and ternary agent e); and
 a second dry powder compositions comprises an admixture of compound c) and carrier excipient d).

14. The pharmaceutical combination product of claim 12, wherein the carrier excipient in said first and second dry powder compositions is lactose monohydrate, and the ternary agent in said first dry powder composition is magnesium stearate.

15. The pharmaceutical combination product of claim 13, wherein said first and second dry powder compositions are in unit dose form and in the form of a capsule, a cartridge or a blister.

16. The pharmaceutical combination product according to claim 12, in a dry powder composition form suitable for administration by inhalation via a medicament dispenser selected from a reservoir dry powder inhaler, a unit-dose dry powder inhaler, or a pre-metered multi-dose dry powder inhaler.

17. The pharmaceutical combination product according to claim 15, in a dry powder composition form suitable for administration by inhalation via a medicament dispenser selected from a unit-dose dry powder inhaler, or a pre-metered multi-dose dry powder inhaler.

* * * * *